(12) United States Patent
Longo et al.

(10) Patent No.: US 7,988,619 B2
(45) Date of Patent: Aug. 2, 2011

(54) DIAGNOSTIC DEVICE FOR TUBULAR ANATOMICAL STRUCTURES

(75) Inventors: Antonio Longo, Palermo (IT); Jesse J. Kuhns, Cincinnati, OH (US); Federico Bilotti, Rome (IT); Michele D'Arcangelo, Rome (IT); Christopher J. Hess, Cincinnati, OH (US); William Bruce Weisenburgh, II, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 921 days.

(21) Appl. No.: 11/662,032

(22) PCT Filed: Jun. 16, 2005

(86) PCT No.: PCT/IT2005/000345
§ 371 (c)(1),
(2), (4) Date: Jun. 28, 2007

(87) PCT Pub. No.: WO2006/046263
PCT Pub. Date: May 4, 2006

(65) Prior Publication Data
US 2007/0249989 A1    Oct. 25, 2007

(30) Foreign Application Priority Data

Oct. 29, 2004 (IT) .............................. MI2004A2079

(51) Int. Cl.
*A61B 1/04* (2006.01)
*A61M 29/00* (2006.01)

(52) U.S. Cl. .................. 600/114; 606/198; 606/191

(58) Field of Classification Search .................. 600/115, 600/116, 219, 223, 114; 604/104–109, 132, 604/164.01, 165.01–165.04, 166.01; 606/41, 606/190, 198, 205–209, 110, 113, 114, 126–127, 606/191
See application file for complete search history.

(56) References Cited

U.S. PATENT DOCUMENTS

| 5,339,803 | A * | 8/1994 | Mayzels et al. ............... 600/201 |
| 6,451,042 | B1 | 9/2002 | Bonutti |
| 2004/0082969 | A1* | 4/2004 | Kerr .............................. 606/205 |
| 2005/0070764 | A1* | 3/2005 | Nobis et al. ................... 600/131 |

FOREIGN PATENT DOCUMENTS

| DE | 852277 C | 10/1952 |
| DE | 19828099 A1 | 12/1999 |
| EP | 1518492 A | 3/2005 |
| JP | 61-280872 A | 12/1986 |
| WO | WO 2005/048828 A | 6/2005 |

* cited by examiner

*Primary Examiner* — Thomas J Sweet
*Assistant Examiner* — Ryan Henderson

(57) ABSTRACT

A diagnostic device for pathologies of tubular anatomical structures comprises a tubular elongated structure having a proximal end and a distal end. The distal end is suitable to be inserted in the tubular anatomical structure. The device includes a means for locally dilating the walls of the tubular anatomical structure that are associated with the distal end of said elongated structure. The means for locally dilating is movable between a closed position for introducing the device and at least one open position for viewing and evaluating the pathology. The device also has a control means on the proximal end of the elongated structure. The control means is operatively connected to the means for locally dilating, in order to move them between the closed position and the open position, and vice versa.

22 Claims, 8 Drawing Sheets

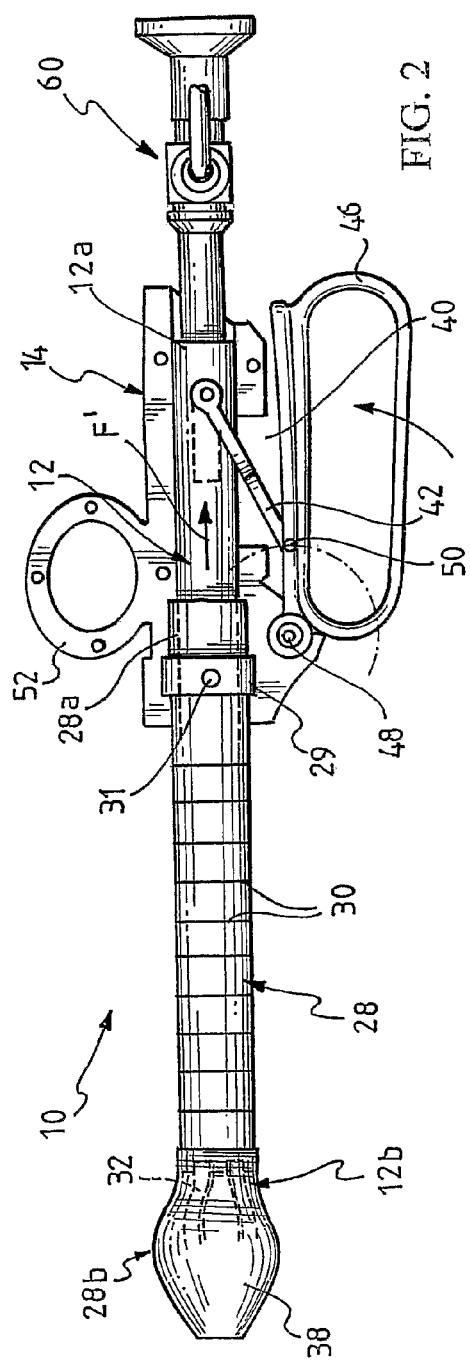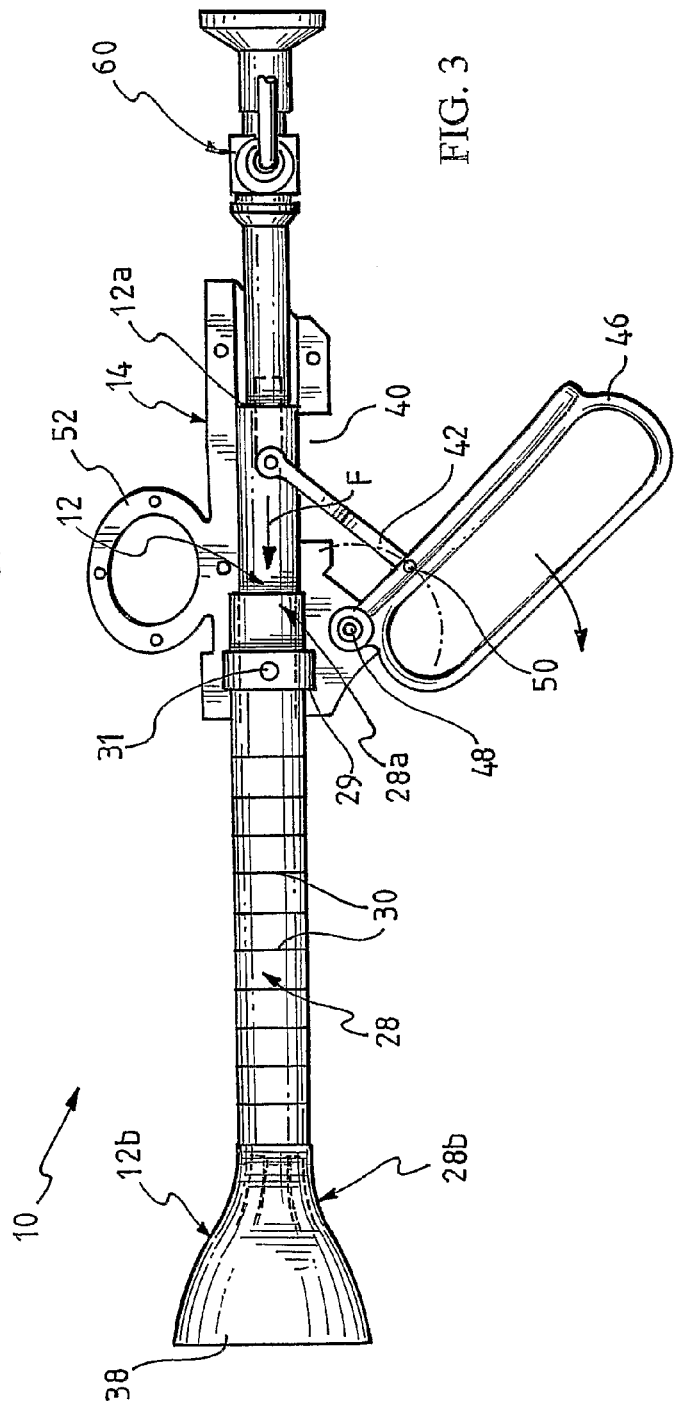

US 7,988,619 B2

DIAGNOSTIC DEVICE FOR TUBULAR ANATOMICAL STRUCTURES

FIELD

A diagnostic device for the pathologies of tubular anatomical structures, such as for example the intestinal tracts, is the object of the present invention. In particular, the present invention relates to a diagnostic device for pathologies of the colon or the rectum such as for example intussusception, stenosis, prolapse, rectocele.

BACKGROUND

The need for the availability of a diagnostic device for the aforementioned pathologies, which can be manufactured with limited expense, usable even in non hospital or clinical structures and which gives rise to the least possible discomfort in patients, avoiding for example the administration of sedatives, is particularly felt within the field. Furthermore, the need for the availability of a diagnostic device which allows the verification of the presence and the extent of a mucosal prolapse is particularly felt.

Diagnostic devices, such as flexible colonoscopes and sigmoidoscopes which have significant drawbacks are known. Generally, colonoscopes work by the insufflation of air in order to dilate the walls of the intestinal tract subjected to analyses. The insufflation of air gives rise to significant discomfort in the patients and frequently it is necessary to resort to the administration of sedatives. Furthermore, the insufflation of air causes dilation of the rectum with the consequence that any possible mucosal prolapse disappears and may not be viewed.

Anoscopes which allow the direct vision of the area involved and which can also be of large dimensions, for example with diameters greater than 2 cm, are also known, causing pain during insertion and requiring the relaxation of the sphincter.

Due to the complexity and the expense of the equipment required, in addition to the high discomfort which they cause in patients, frequently the only structures which are so equipped are hospitals or clinics, requiring therefore that the majority of the diagnostic procedures be carried out in such environments.

The problem at the heart of the present invention is that of providing a diagnostic device for the pathologies of the intestinal tracts, in particular of the rectum and colon, which has structural and operational characteristics such as to satisfy the aforementioned needs and to overcome the aforementioned drawbacks cited in reference to the known art.

Such a problem is solved by a diagnostic device in accordance with claim 1. The dependent claims refer to further embodiments of the device according to the present invention.

Further characteristics and advantages of the diagnostic device according to the invention will arise from the following reported description of its preferred exemplary embodiments, which are given as non-limiting indication, with reference to the attached figures, wherein:

DESCRIPTION OF THE DRAWINGS

FIG. 2 shows a side view of the diagnostic device from FIG. 1, where several details have been omitted in order to enhance other ones;

FIG. 3 shows the diagnostic device from FIG. 2 in a different operating condition;

DETAILED DESCRIPTION

The present invention generally relates to a diagnostic device for pathologies of tubular anatomical structures, such as the intestinal tracts for example of the rectum and colon. In general terms the device advantageously comprises an elongated structure which develops between a proximal end and a distal end and which is suitable for being inserted within the anatomic structure to be examined. Means for locally dilating the walls of the tubular structure associated with the distal end of the elongated structure are further provided. The means for dilating are movable between a closed position for the introduction of the device and at least one open position for the viewing and the evaluation of the pathology.

The means for locally dilating are operatively connected with control means associated with the proximal end of the elongated structure. These control means are actuated by the operator in order to open or close the dilating means.

In addition, viewing means suitable for being associated with the elongated structure and for reaching the tract dilated by the means of dilating are provided.

In general terms, which can be applied to any embodiment of the device according to the present invention, by proximal is conventionally meant either a portion or end of the device which, whilst in use, is near to the operator holding the device and carrying out the examination, whereas by distal is conventionally meant either a portion or end of the device which, whilst in use, is remote with respect to the operator carrying out the examination. Furthermore, by the term advancement is meant a movement, preferably translation, carried out in the direction from the proximal end towards the distal end (for example along the arrow F of FIG. 3), whereas by withdrawal is meant a movement, preferably translation, carried out in the direction from the distal end towards the proximal end (for example along the arrow F' of FIG. 2).

Some embodiments of such a device will be described below, for example with reference to the annexed figures.

Figure 1:
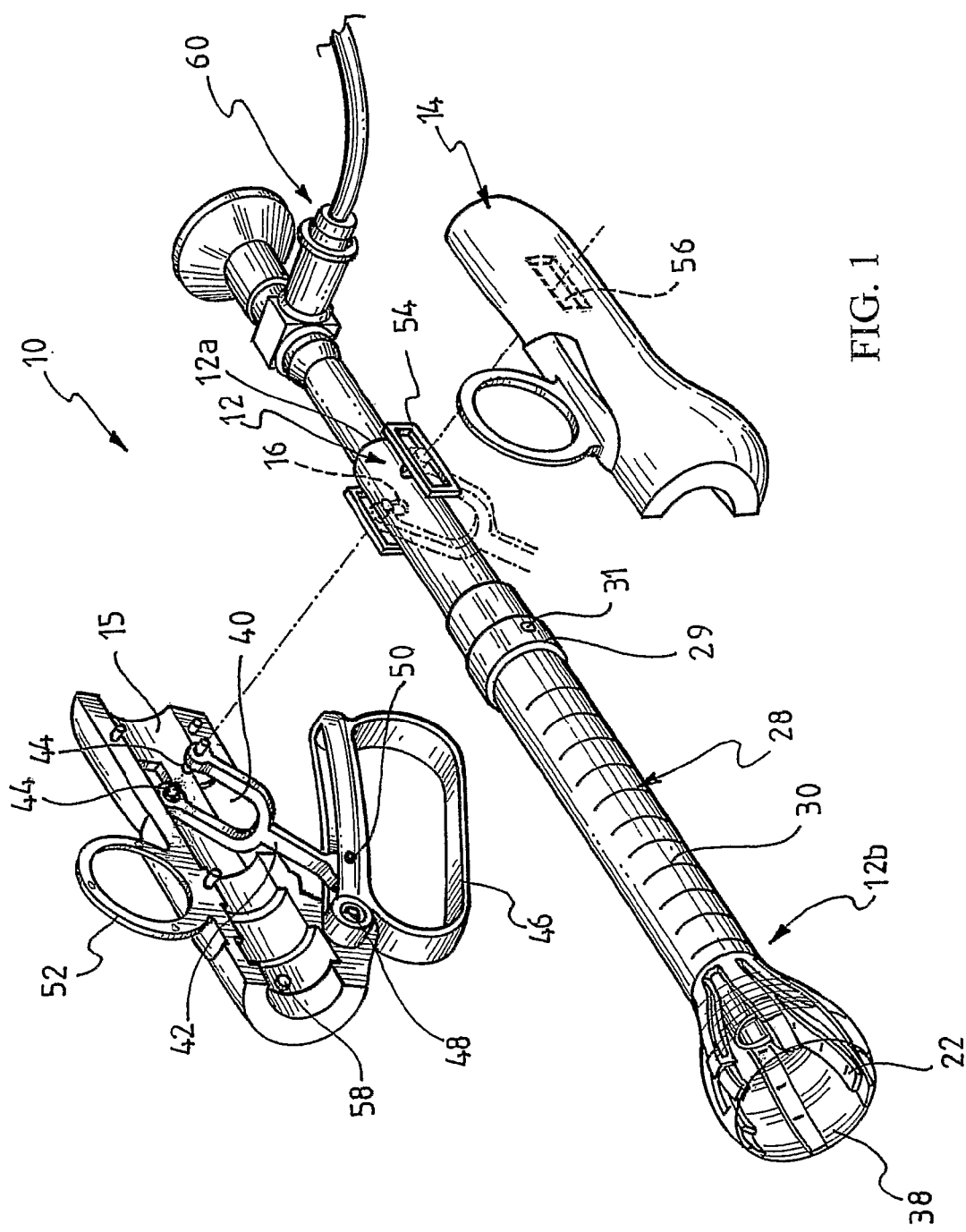
FIG. 1 is an exploded, perspective view of a possible embodiment of the diagnostic device according to the present invention.

With reference to the FIGS. 1-3, by 10 has been generally indicated a trans-anal diagnostic device according to a first embodiment. The elements in common throughout the illustrated embodiments will be described and designated with the same numeral.

With 12 has been designated an inner tube preferably of a cylindrical shape and hollow inside. The inner tube 12 may be for example in semi-rigid or flexible material, for example in plastic material.

The inner tube 12 extends between a proximal end 12a and a distal end 12b. The proximal end 12a is operatively associated with a grip member 14, for example in the shape of a handle. More in particular, the inner tube is partially housed within a cylindrical cavity 15 of the grip member 14 and is free to slide therein along its longitudinal axis.

According to a possible embodiment, two slots 16 are formed in portions that are diametrically opposed to the inner tube 12 and near the proximal end 12a. More in particular, the slot 16 extends in the circumferential direction relative to the inner tube 12. Preferably both slots pass through the entire thickness of the inner tube 12.

The distal end 12b of the inner tube is operatively linked to arms or petals 22 preferably extending in the longitudinal direction relative to the inner tube 12. Advantageously, the arms 22 are formed as one piece with the inner tube 12. A possible embodiment of the arms 22 will be described below with reference to FIGS. 4-6.

Figure 4:
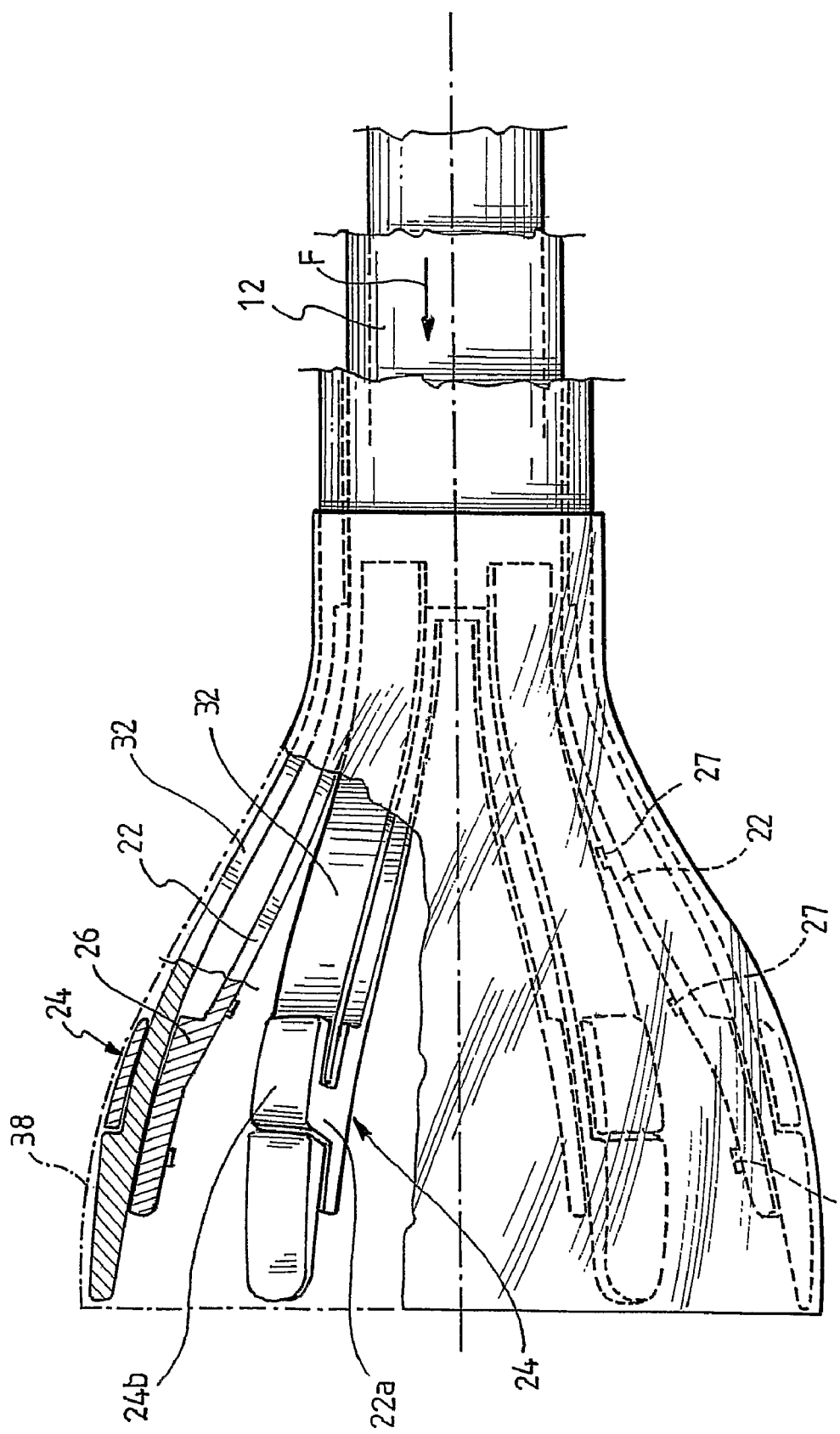
FIG. 4 shows a perspective view of a detail of the distal end of a diagnostic device according to the present invention, in accordance with a possible embodiment and in a first operating condition.
Figure 5:
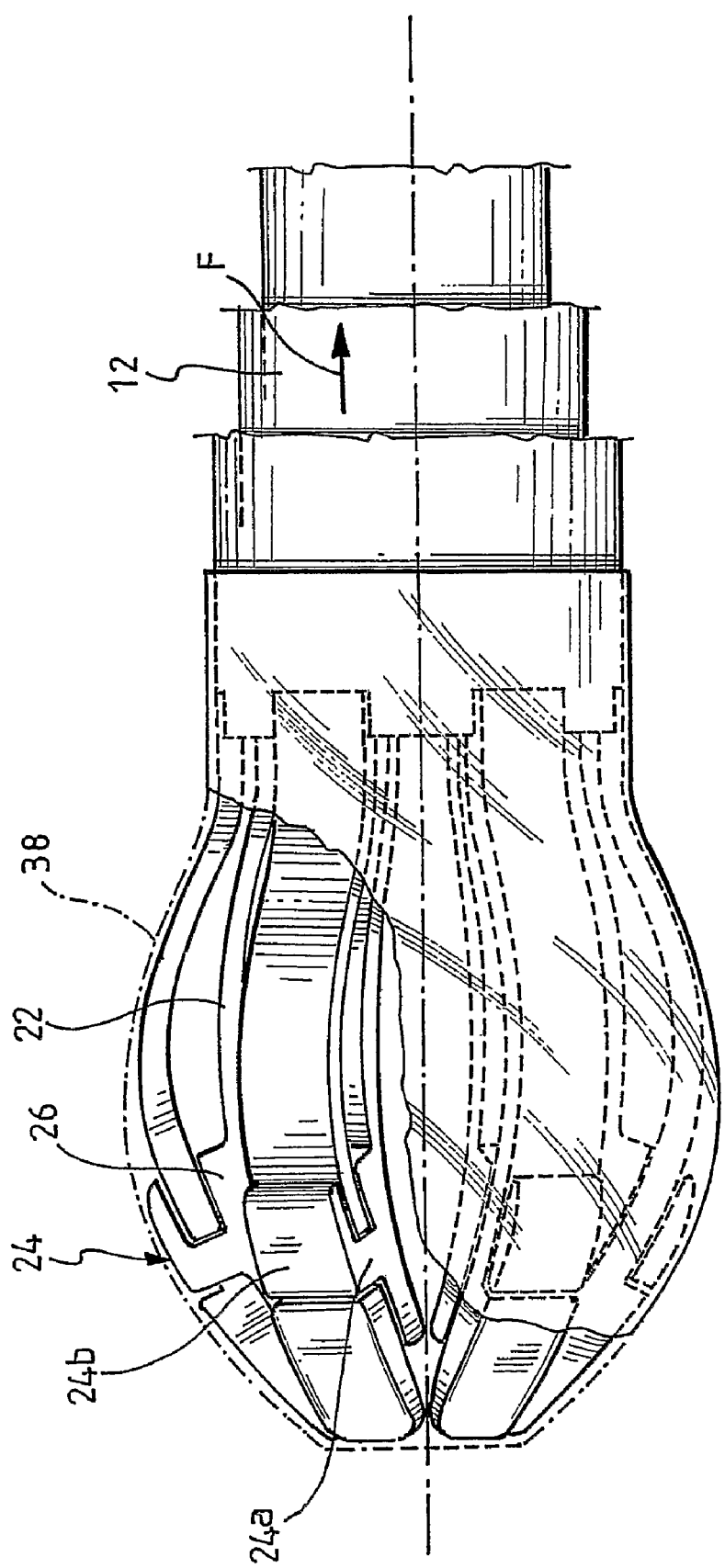
FIG. 5 shows a perspective view of the detail from FIG. 4 in a second operating condition.
Figure 6:
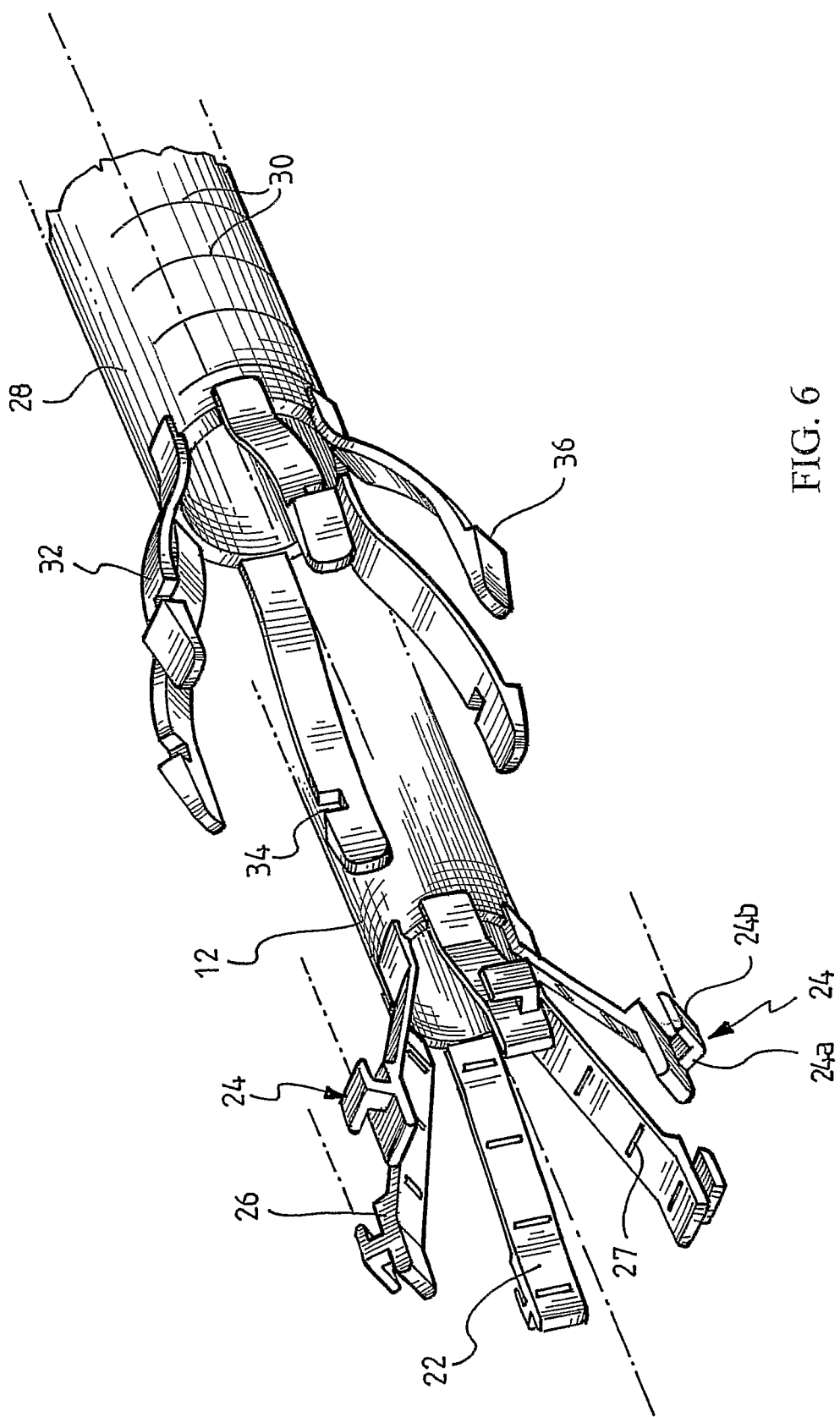
FIG. 6 illustrates an exploded, perspective view of two components of the detail from FIG. 4 or 5.

FIGS. 4-6, in fact, show an enlarged detail of the distal end of the diagnostic device.

In accordance with a possible embodiment, an arm 22 of the inner tube 12 comprises a hook 24 extending out of the arm, in a substantially radial direction. More in detail, the hook 24 has an L-configuration extending from one side of arm 22 and runs down the arm in a crosswise manner. In other words, the hook 24 defines a seat being laterally opened on arm 22. Yet in other words, the hook 24 comprises a first tract 24a extending from the arm 22 perpendicular thereto and towards the exterior of the arm, and a second tract 24b extending perpendicular to the first one crosswise to the longitudinal development of the arm 22. Preferably, the length of second tract as measured along the longitudinal direction of arm 22 is greater than that of the first tract. Furthermore, the second tract preferably extends along a width, as measured crosswise to the longitudinal direction of the arm, which is equal to about the width of the arm.

In accordance with a possible embodiment, the free end 22a of the arms has an enlargement 26 such as to have a greater thickness than the remaining portion of the arm. Advantageously, the enlargement 26 is arranged at the hook 24.

The arms 22 are suitable to assume at least two extreme configurations corresponding to a closed configuration (FIG. 5) and completely open configuration (FIG. 4). In the closed configuration, the free ends of the arms 22 are in contact to each other and the tip or distal end of the diagnostic device is substantially olive-shaped. In the open configuration, the arms 22 mutually detach and assume a configuration which is substantially cup-shaped.

In accordance with a possible embodiment, at least one of the arms 22 has detection elements or markers 27 therein, which are preferably numerated along the longitudinal direction of the arm in order to evaluate the extent of the pathology encountered.

With reference to the embodiment illustrated in FIGS. 1-3, an outer tube has been overall designated with 28. In the assembled configuration of the device 10, the outer tube 28 houses the inner tube 12 therein. With reference also to the outer tube 28 a proximal end designated with 28a and a distal end designated with 28b can be identified. According to a possible embodiment, the outer tube 28 can be made of semi-rigid or flexible material, for example of plastic material.

According to a possible embodiment, the outer tube 28 may have one or more detection elements or markers 30, for example distributed along the length of the outer tube itself, in order to measure the length of penetration of the device inside the anus and accordingly the location of the pathology encountered.

According to one possible embodiment the markers 30 have the shape of circular rings that are arranged transversal to the tube, which are preferably numerated and distributed along the length of the outer tube.

In accordance with a possible embodiment, the proximal end 28a of the outer tube has an annular rib 29. In accordance with a further embodiment, the proximal end 28a of the outer tube has at least one hole 31, preferably two holes that are arranged diametrically opposed on the outer tube and preferably passing through the thickness of the outer tube. In the event that both the annular rib 29 and the holes 31 are advantageously provided, the latter are formed at the annular rib.

Advantageously, the outer tube 28 is shorter than the inner tube 12 such that a portion of the inner tube starting from the proximal end of the inner tube projects from the proximal end of the outer tube, for example within the cylindrical cavity 15 of the grip member 14.

In accordance with a possible embodiment, the outer tube and the inner tube are partially housed within the grip member 14, more precisely within the cylindrical cavity 15.

The distal end 28b of the outer tube is operatively linked to arms or petals 32 preferably extending in the longitudinal direction relative to the outer tube 28. Advantageously, the arms 32 are formed as one piece with the outer tube 28. FIGS. 4-6 show in detail a possible embodiment of the arms 32 of the outer tube.

To each arm 22 of the inner tube 12 there corresponds an arm 32 of the outer tube 28, and in the assembled configuration of the device 10, the two associated arms overlap.

In accordance with a possible embodiment, the arms 22 of the inner tube 12 and the arms 32 of the outer tube 28 have such a configuration suitable to mutual coupling, particularly by means of a shape-coupling that allows to control the opening and closure of the arms 32 of the outer tube 28 by opening and closing the arms 22 of the inner tube 12.

With reference to FIGS. 4-6 and particularly FIG. 6, each arm 32 has a seat 34 on the side thereof which is suitable to receive a portion of the hook 24 and particularly the first tract 24a. Furthermore, the distal end of the arms 32 has a step 36 suitable to abut against the hook 24, and particularly against the second tract 24b.

The mutual assembly of the arms 22 of the inner tube 12 and the arms 32 of the outer tube 28 provides that one tube is inserted inside the other such that the respective arms are slightly angularly offset. A slight mutual rotation of the two tubes will bring each arm 32 of the outer tube into the seat being defined by the respective hook 24. The seat 34 houses the first tract 24a whereas the second tract 24b abuts against the step 36.

Preferably, the thickness of step 36 decreases towards the free end of the arm 32.

The arms 32 of the outer tube 28 are suitable for assuming at least two extreme configurations corresponding to a closed configuration (FIG. 5) and a completely open configuration (FIG. 4). In the closed configuration, the free ends of the arms 32 are in contact to each other and the tip or distal end of the diagnostic device is substantially olive-shaped. In the open configuration, the arms 32 mutually detach and assume a configuration which is substantially cup-shaped.

The passage between the two open/closed extreme positions of the distal end of the device is carried out by means of a relative translation of the inner tube 12 and the outer tube 28. Advantageously, the arms 32 of the outer tube 28 are idle and controlled by the arms 22 of the inner tube both for opening and closing.

Considering the stationary outer tube and the moving inner tube, by making the inner tube advance along the arrow F one passes from the closed configuration (FIG. 5) to the open configuration (FIG. 4). In fact, both the first tract 24a and the second tract 24b push each arm 32 of the outer tube to a radially wider position. On the contrary, a backward movement of the inner tube along the arrow F' causes the arms 22 of the inner tube and 32 of the outer tube to shift from the open configuration (FIG. 4) to the closed configuration (FIG. 5). In fact, the first tract 24a of the hook 24 cooperates with the arm 32 of the outer tube 28, within the seat 34, whereas the second tract 24b cooperates with the outer surface of the arm 32 by dragging each corresponding arm 32 of the outer tube 28 to closure.

According to a possible embodiment, a membrane 38 preferably made from plastic or foldable material is fit on the distal end of the outer tube 28, i.e. on the arms 32. According to a possible embodiment, the membrane is made from transparent material.

FIGS. 1-3 show a possible embodiment of the means for actuating a relative translation movement between the inner tube 12 and the outer tube 28. Specifically, these means are suitable for translating the inner tube 12 relative to the stationary outer tube 28, but it may also be provided otherwise.

The grip member 14 has an elongated opening 49 allowing the connection between the inner tube 12 and a control slide 42. Preferably, the control slide is fork-shaped in order to be connected to the inner tube at portions diametrically opposed thereon.

Particularly, the control slide 42 has ends that are suitable to be inserted in the slots 16 of the inner tube, from the outside of the inner tube. In the case where the control slide is fork-shaped, the ends of the prongs comprise relative pins 44 which are suitable to be inserted into the slots 16.

A control member 46 is operatively associated with the control slide 42 to generate a forward and backward motion of the inner tube within the outer tube.

Advantageously, the control member 46 is configured as a lever with an end connected to the grip member 14 by means of a pin 48. The connection between the control member 46 and the control slide 42 is provided by a further pin 50 that is mounted on the control member 46 in an intermediate area between the pin 40 and the free end of the control member 46.

In accordance with a possible embodiment, the grip member 14 comprises a ring 52 to receive the thumb of the operator's hand.

According to an advantageous embodiment, besides to what has been described above, there is provided a guide profile 54 which is housed in a longitudinal groove 56 of the grip member 14. The pins 44 also extend outside the inner tube for being inserted into the guide profile 54.

In accordance with a possible embodiment, the cylindrical cavity 15 of the grip member 14 is counter-shaped relative to the annular rib 29 of the outer tube such as to prevent that the outer tube may translate within the grip member 14. Furthermore, the cylindrical cavity 15 may have pins 58 suitable to be inserted in the holes 31, if provided, of the outer tube in order to prevent that the outer tube may rotate within the grip member 14.

With reference to the embodiment illustrated in FIGS. 1-3, the operator holds the grip member 14, by passing his thumb through the ring 52, if present, and gripping the control member 46.

From the open position from FIG. 1 or 3, the operator rotates the control member 46 by closing the same towards the grip member body. The control slide 42 pushes the inner tube 12 backwards thereby closing the arms of the inner tube and the outer tube such as described above. The pins 44 are free to slide along the slots 16 in the circumferential direction relative to the tube. The cylindrical cavity 15 has such an extension allowing a translation movement of the inner tube that is sufficient for the arms to shift between the two extreme open/closed positions.

With reference to the definition of the device according to the present invention, the inner tube and the outer tube define the elongated structure developing between a proximal end and a distal end. The length of the elongated structure may be changed. As a function of the material with which the inner tube and the outer tube are made, the elongated structure can be either semi-rigid or flexible. The arms 22 of the device 10 define means for locally dilating the walls of the anatomical structure of interest, which are associated with the distal end of the elongated structure. The control means comprise the inner tube and the outer tube which can slide one inside the other and the means which cause this relative translation.

The device 10 in the closed position is introduced transanally into the rectum/colon sigmoid/colon of the patient by the physician or the operator carrying out the examination. The degree of introduction of the device 10 can be verified using the markers 30 on the outer tube 28, if present. The insertion of the device 10 is facilitated by the olive-shape of the distal tip of the device, i.e. of the arms 22 and 32.

When the desired position has been reached, the distal end of the device is opened "flower-like" such as to gradually widen the area of interest, as will be described below with reference to the embodiment in question.

The operations described above for opening the distal end of the device 10, in which a translation of the inner tube 12 is provided to be generated relative to the grip member 14 and outer tube 28, can be similarly carried out by generating a translation of the outer tube relative to the inner tube and grip member.

The device 10 described above may be used in association with viewing equipment (for example laparoscopes 60) which are introduced into the inner tube 12 and which, thanks to the opening of the arms 22, can be directed towards the appropriately widened area of interest such that the operator (physician) can check for the presence and the extent of the various pathologies. In other words the inner tube 12 allows the passage of illuminating and optical elements for the viewing of the area of interest.

Alternatively, the device 10 can be associated with an apparatus provided with a colon-scope and insufflation device available from specialist medical practitioners.

By gradually and selectively widening the distal end of the device 10, for example, one can check the response of the mucosa by mimicking defecation.

The present device allows the diagnosis of various pathologies among which intussusception, stenosis, prolapse, rectocele. The location of the defect can be quantified by means of the markers arranged on the outer tube. The extent of the defect can be quantified as a function of the location to which the mucosa falls along the markers on the arms.

The device 10 can additionally be moved backwards or forwards while opening and closing the same in order to allow the analyses of the various sections of tissues and in order to diagnose the conditions of the prolapse.

From what has been stated above, one can appreciate how providing a diagnostic device according to the present invention allows to have available a low cost device useful in the diagnosis of pathologies of tubular anatomical structures such as colon-rectal tracts. For example it is possible to identify and evaluate pathologies like intestinal blockages, intussusception, stenosis, prolapse and rectocele.

Being capable of carrying out the diagnosis and quantification of a rectal prolapse is particularly advantageous, since the known devices, particularly colonoscopes, do not allow the diagnosis of such a pathology. Indeed colonoscopes require insufflation of air which causes rectal dilation and consequently the disappearance of the mucosal prolapse.

In addition to what has been described above, the diagnostic device according to the present invention reduces patient's discomfort and can be used even without the administration of sedatives, being much easier to introduce with respect to the known devices and does not require the insufflation of air.

An additional advantage of the diagnostic device according to the present invention is linked to the small size in which it can be made, eliminating the drawbacks of the direct vision anoscopes which are painful and require the relaxation of the sphincter in that they have rather large dimensions.

In addition to what has been stated above, the diagnostic device according to the present invention can also be used on an outpatient basis, or in any case in non hospital or clinical environments, being a simple structure, easy to use and having a low cost, and which does not require the administration of sedatives.

In particular providing a tip or head or distal end which is non traumatic both during insertion in the closed position and during use in the open position is particularly advantageous.

Furthermore, the risk that the tissue may sag or be caught in the jaws of the device is minimized or even eliminated.

The variety of materials with which both the inner tube and the outer tube can be made also allows the attainment of a relatively flexible elongated structure, adapted to being easily introduced in particular up to the sigmoidal colon.

The use of markers, both on the outer tube and on the arms allow respectively to quantify the depth of insertion of the device and to quantify the prolapse.

The conformation of the device allows, in the closed position, the limiting of the risk that extraneous elements may introduce themselves into the interior of the device itself.

The shape reached in the completely open position is particularly advantageous for initiating a response from the sphincter. In addition, the shape of the arms is preferably designed such as to have maximum radial opening at the distal end of the device.

It should be understood that variations and/or additions to what has been described and illustrated above may be provided.

The shape, both of the inner tube and the outer tube can vary with respect to what has been described and illustrated above. The materials may also be different. For example, the embodiments described above provide idle arms, i.e. both the opening and closing of the arms 22 and 32 are controlled by the operator. By changing the materials, one may obtain a device in which the arms are naturally open and the shifting between the closed and open positions mainly occurs by elastic effect after the physician has left the inner tube slide freely within the outer tube.

The shape-coupling between the arms of the inner tube and outer tube can be different. For example, either the step 36 or tract 24b may be omitted.

The distal end of the device, i.e. the configuration of the arms 22 and 32 may also be associated with other types of command or control of the translation of the inner tube 12 relative to the outer tube 28. For example, there may be used similar commands as those that will be described below with reference to further embodiments of the diagnostic device according to the present invention.

Analogously, the command for translating the inner tube 12 relative to the outer tube 28 may be used with different embodiments of the distal tip.

Figure 7:
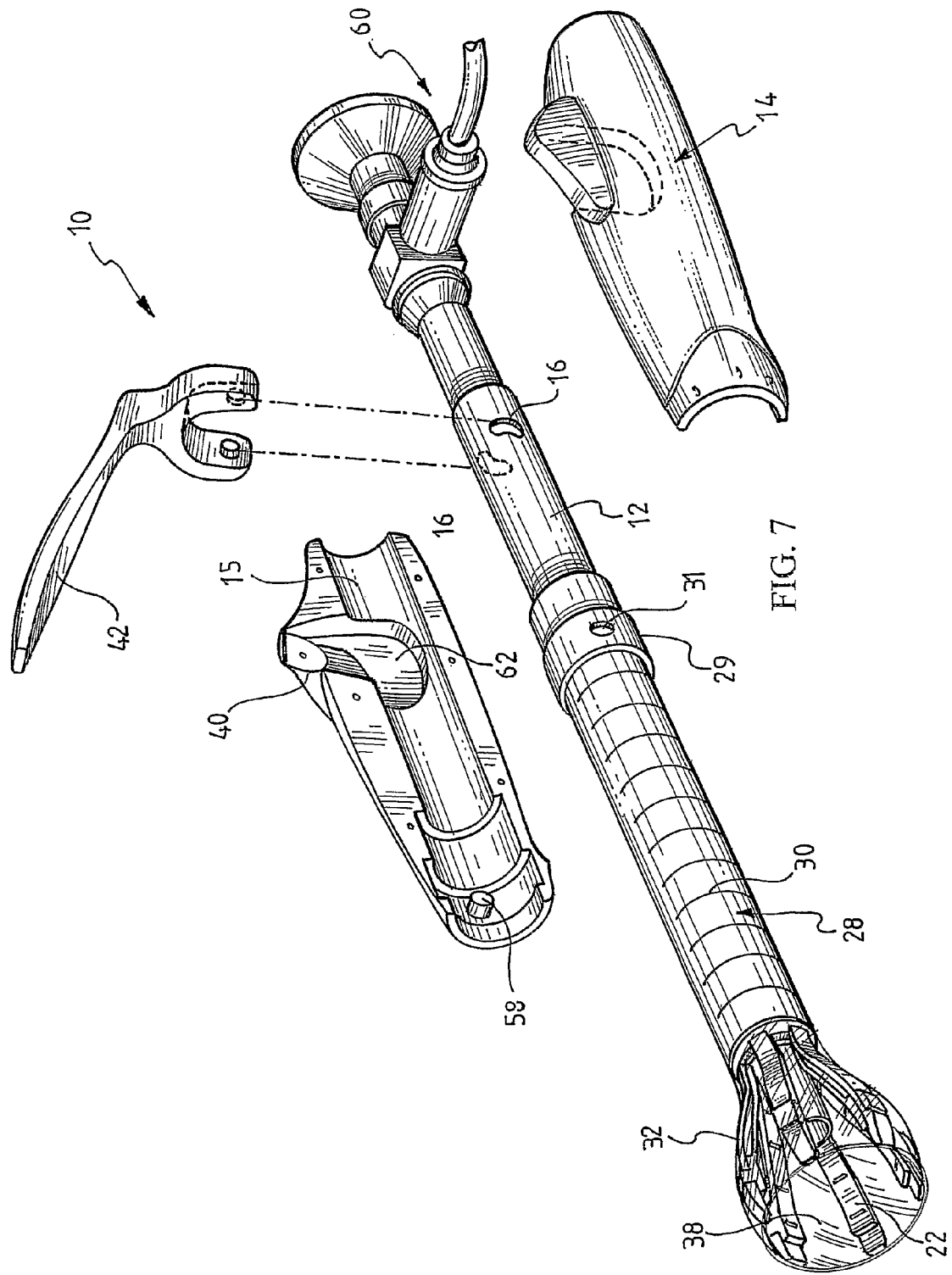
FIG. 7 is a partially exploded, perspective view of a possible embodiment of the diagnostic device according to the present invention.
Figure 8:
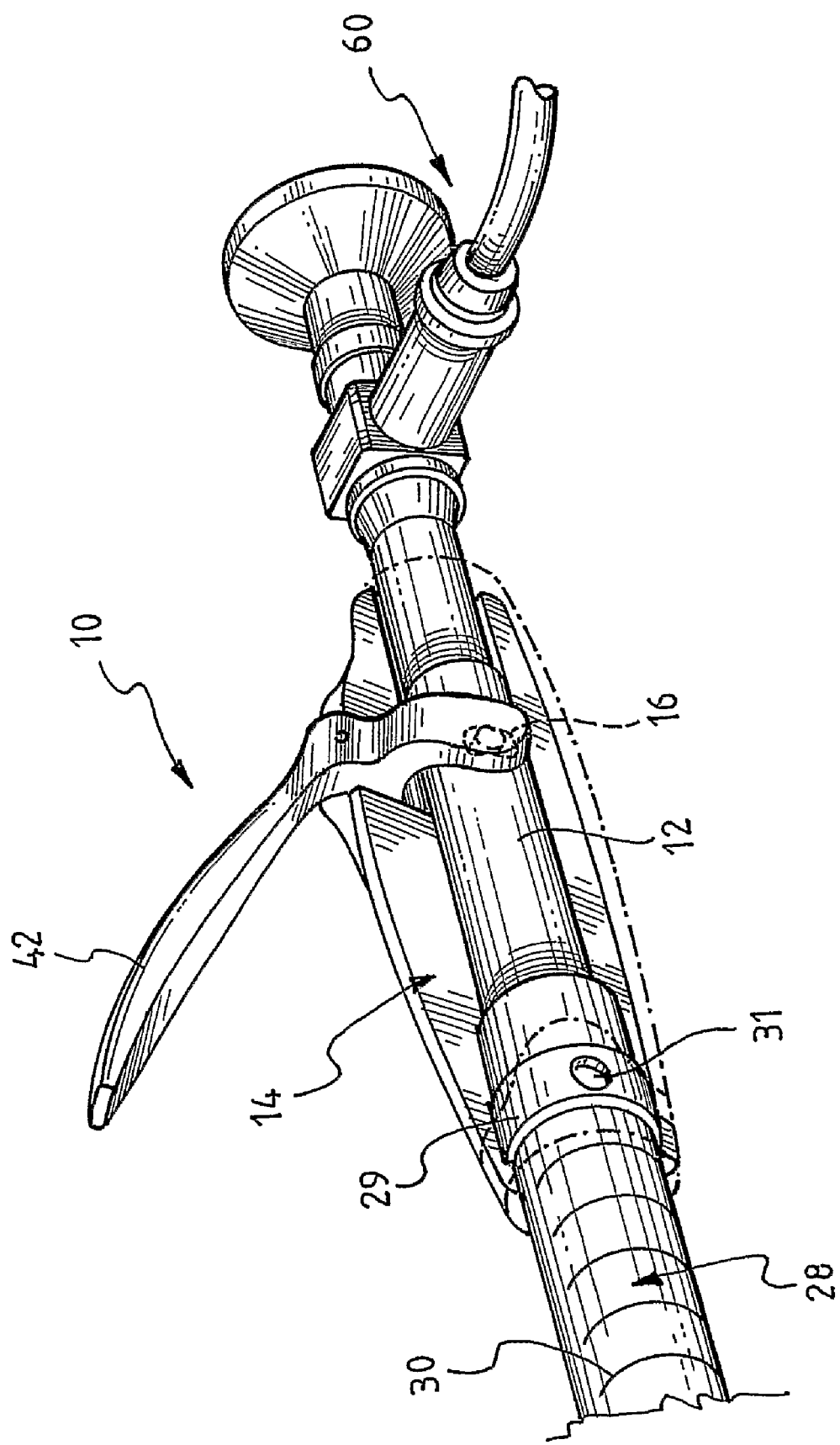
FIG. 8 shows a perspective view of a detail of the diagnostic device from FIG. 7, when assembled, where several details have been omitted in order to enhance other ones.

FIGS. 7 and 8 show a possible embodiment of the diagnostic device 10. Particularly, FIGS. 7 and 8 show a possible embodiment of the means generating a relative translation between the inner tube and the outer tube. The elements in common with the above embodiments have been designated with the same numerals.

The cylindrical cavity 15 of the grip member 14 is counter-shaped relative to the annular rib 29 of the outer tube and advantageously has the pins 31 which are suitable to be inserted into the holes of the outer tube. The translation and rotation movement of the outer tube relative to the grip member are then prevented.

The translation of the inner tube relative to the outer tube and grip member is controlled by a control slide 42 which is suitable to be pivoted to the grip member and interact with the inner tube. The control slide 42 is housed in the grip member 14 by being inserted in an aperture 40.

Particularly, the control slide 42 is forked-shaped. The free ends of the prongs are suitable to be inserted in the slots 16 of the inner tube. Advantageously, the control slide 42 is pivoted to the grip member in an intermediate area between the prong ends and the free end of the control slide.

The cylindrical cavity 15 of the grip member 14 has a notch 62 allowing the rotation of the control slide 42.

The method for employing the embodiment of the above diagnostic device is described below. In general terms, it is similar to that of the embodiment described above. In other words, the relative translation of the inner tube and the outer tube gradually change the configuration of the distal end of the device from a closed configuration to a completely open configuration and vice versa.

In the embodiment described below, the relative translation between the inner tube and the outer tube is obtained by rotating the control slide 42 relative to the grip member being held by the operator. The control slide 42 acts directly on the inner tube 12 thereby causing the same to rotate relative to the grip member and the outer tube, either forwards or backwards, (arrows F and F') as a function of the direction of rotation of the control slide 42.

Depending on the materials, the opening of the arms may be either directly controlled by the physician or affected by the elasticity of the material.

The advantages discussed above also find validity in the further embodiment described above. It should be understood that variations and/or additions to what has been described and illustrated above may be provided.

Also in this case, it may also be provided that the outer tube translates relative to the inner tube.

The means suitable to generate the relative translation movement between the inner tube and the outer tube as described with reference to the FIGS. 7-8 can be used with any embodiment of the distal end of the device, particularly the arms 22 and 32. For example, they can be used with the embodiment shown in FIGS. 4-6 or any other embodiment.

Figure 9:
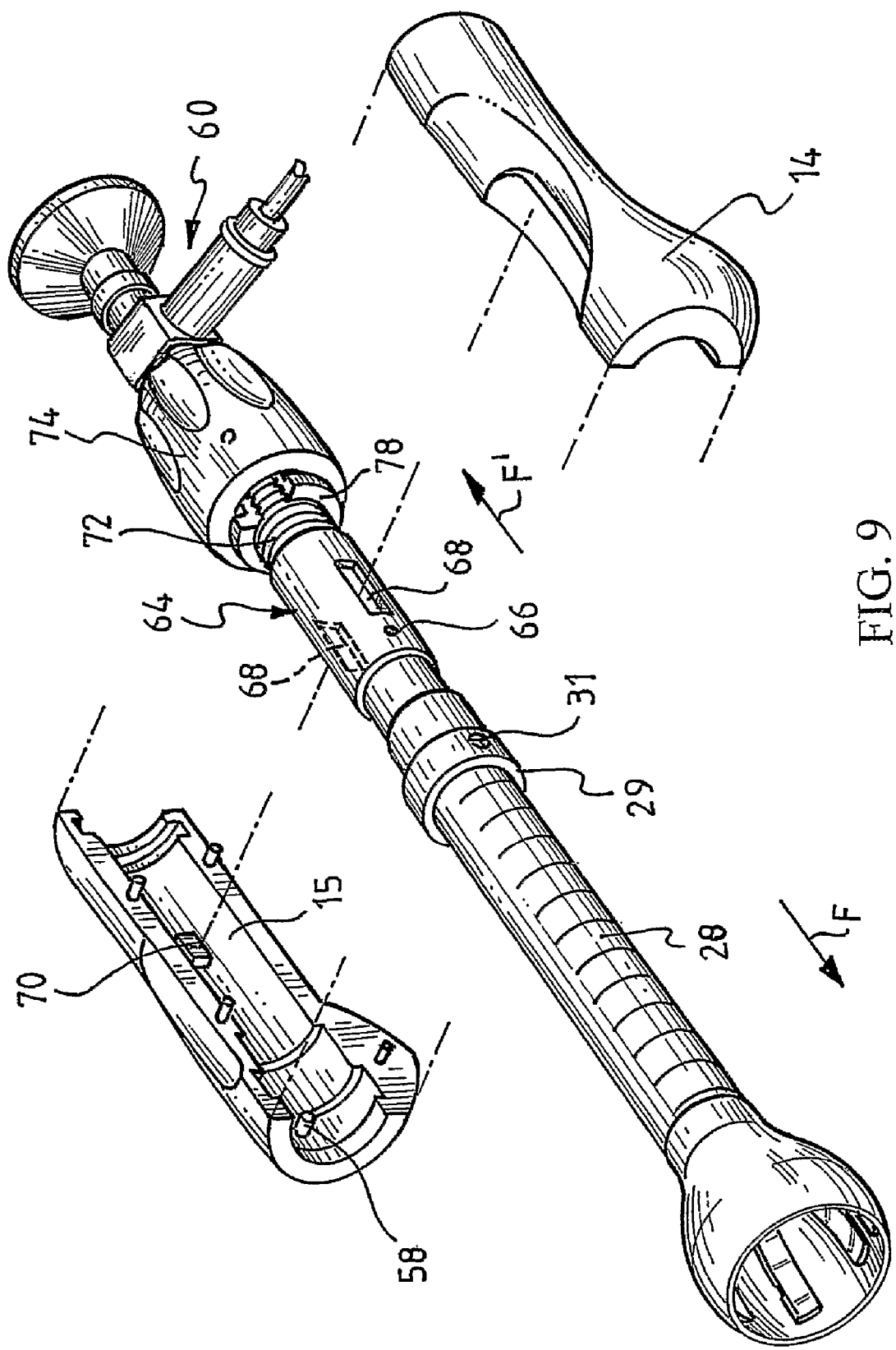
FIG. 9 is a partially exploded, perspective view of a possible embodiment of the diagnostic device according to the present invention.

FIG. 9 shows a possible further embodiment of the diagnostic device according to the present invention. For clarity purposes, the elements in common with the above embodiments will be designated with the same numerals.

The structure of the outer tube and the coupling thereof with the grip member 14 are substantially similar to what has been described above.

The inner tube 12 comprises an end portion 64 that is fitted on the proximal end of the inner tube. A pin 66 is inserted crosswise between the inner tube and the end portion thereby making the same integral to each other. The end portion has at least one groove 68 extending along the longitudinal direction of the inner tube. Preferably, two grooves 68 are provided which are arranged diametrically opposed to each other on the end portion. The cylindrical cavity 15 has lugs 70 that are suitable to be inserted in the grooves 68 to prevent that the inner tube may rotate. The dimensions of the lugs and respective grooves are such as to allow a relative translation of the inner tube within the outer tube such as to enable the same to shift from the two extreme open/closed configurations.

The proximal end of the end portion 64 has a threaded tract 72.

The grip member 14 comprises a handle 74 that is fitted on the proximal end of the grip member 14 and provided with a threaded tract therein which is suitable to engage with the threaded tract of the end portion.

Preferably, the handle 74 is integral with a ferrule 78 in which the threaded tract is formed.

Also with this embodiment one may use a laparoscope 60 inserted within the inner tube 12 through the handle 74.

With reference to the definition of the device according to the present invention, the inner tube and the outer tube define the elongated structure developing between a proximal end and a distal end. The length of the elongated structure may be changed. Depending on the material with which the inner tube and the outer tube are made, the elongated structure can be either semi-rigid or flexible. The control means comprise the inner tube and the outer tube that can slide one inside the other and the means which cause this relative translation.

The method for employing the embodiment of the above diagnostic device is described below. In general terms, it is analogous to that of the embodiment described above. In other words, the relative translation of the inner tube and the outer tube gradually change the configuration of the distal end of the device from a closed configuration to a completely open configuration and vice versa.

In the embodiment described above, the relative translation of the inner tube within the outer tube is obtained by rotating the handle 74 relative to the grip member being held by the operator. By rotating the handle, the end portion and inner tube translate relative to the grip member and the outer tube either forwards or backwards (arrows F and F') as a function of the direction of rotation of the handle.

The rotation of the inner tube is prevented by the coupling between the lugs 70 of the grip member and the grooves 68 of the end portion.

The relative translation between the inner tube and the outer tube causes the distal end of the device to open or close depending on the embodiment being used. In fact, the means controlling the relative translation between the inner tube and the outer tube as described above can be associated with any means for widening the distal end of the device. For example, similar arms to those described in the embodiment illustrated in FIGS. 4-6 or other embodiments may be provided.

The application mode and method for introduction and visualization are similar to those described above for the first embodiment.

The advantages discussed above also find validity in the further embodiment described above. It should be understood that variations and/or additions to what has been described and illustrated above may be provided.

With reference to all the embodiments that have been shown and described, there may be provided different means suitable to change the configuration of the means for locally dilating the walls of the tubular structure. For example, there may be provided means other than and inner tube and outer tube that can be relatively translated in order to change the configuration of the means for locally dilating the walls of the tubular structure.

To the preferred embodiments of the diagnostic device such as described above, those skilled in the art, aiming at satisfying contingent and specific requirements, may carry out a number of modifications, adaptations and replacement of elements with others functionally equivalent, without however departing from the scope of the claims below.

What is claimed is:

1. A diagnostic device for pathologies of tubular anatomical structures comprising:
   a tubular elongated structure having a proximal end and a distal end and being suitable to be inserted in the tubular anatomical structure,
   means for locally dilating the walls of the tubular anatomical structure that when such structures are adjacent the distal end of said elongated structure, said means for locally dilating being movable between a closed position for the introduction of the device and at least one open position for the viewing and evaluation of the pathology,
   control means being associated with the proximal end of the elongated structure, said control means being operatively connected to said means for locally dilating in order to move them between the closed position and the open position, and vice versa,
   wherein said locally dilating means comprise:
       an inner tube and an outer tube housing said inner tube therein,
       a plurality of inner arms linked to a distal end of said inner tube and a plurality of outer arms linked to a distal end of said outer tube,
   wherein each one of said inner arms is coupled to respectively one of said outer arms by means of detachable shape-coupling such that a translation of the inner tube with respect to the outer tube moves the outer arms from said closed position to said open position and vice versa, wherein said inne and outer arms radially expand when transitioned from said closed position to said open position,
   wherein said inner tube with said inner arms is insertable in said outer tube with said outer arms and a rotation of the inserted inner tube with respect to the outer tube moves said inner arms from a detached angularly offset position with respect to the outer arms to an overlapping position with the outer arms, thereby creating said shape coupling.

2. The diagnostic device according to claim 1, further comprising viewing means suitable to be associated with the elongated tubular structure and reach the tract of the tubular anatomical structure being dilated by the dilating means.

3. The diagnostic device according to claim 2, wherein the elongated tubular structure is internally hollow in order to receive the viewing means.

4. The diagnostic device according to claim 1, wherein said locally dilating means comprise arms that are associated with an inner tube and arms that are associated with an outer tube housing said inner tube therein, said arms associated with the outer tube and said arms associated with the inner tube being coupled to each other by means of shape-coupling such that to a relative translation of the inner tube and outer tube there corresponds an opening or closure of the arms,
   wherein a distal translation of the inner tube with respect to the outer tube opens the outer arms, thereby detaching distal free ends of said outer arms, and a proximal translation of the inner tube with respect to the outer tube closes the outer arms, thereby bringing said distal free ends of said outer arms in contact to one another.

5. The diagnostic device according to claim 4, wherein the distal end of the inner tube is operatively associated with said inner arms that are formed as one piece with the inner tube.

6. The diagnostic device according to claim 5, wherein each one of said inner arms of the inner tube comprises a hook extending towards the exterior of the inner arm, which is suitable to receive a coupling portion of respectively one of the outer arms of the outer tube.

7. The diagnostic device according to claim 6, wherein the hook has an L-configuration extending from one side of the inner arm and runs down the inner arm in a crosswise manner.

8. The diagnostic device according to claim 7, wherein the hook defines a seat being laterally opened on the inner arm in order to receive the outer arm of the outer tube.

9. The diagnostic device according to claim 8, wherein the hook comprises a first tract extending from the inner arm in the perpendicular direction thereto and towards the exterior of the inner arm, the first tract being suitable to be inserted in a seat of the outer arm of the outer tube.

10. The diagnostic device according to claim 9, wherein the hook comprises a second tract extending perpendicular to the first tract in the cross-direction relative to the inner arm, said second tract being suitable to abut against a step of the outer arm of the outer tube.

11. The diagnostic device according to claim 10, wherein the distal end of the outer tube is operatively associated with said outer arms that are formed as one piece with the outer tube.

12. The diagnostic device according to claim 1, further comprising a means for generating a relative translation between the inner tube and the outer tube within a grip member.

13. The diagnostic device according to claim 12, wherein said means for generating a relative translation comprises a control slide having an end connected to the inner tube to control the translation thereof within the outer tube.

14. The diagnostic device according to claim 13, wherein said control slide is fork-shaped, wherein prongs of said fork are connected to said inner tube.

15. The diagnostic device according to claim 14, wherein the prongs of said fork are suitable to be inserted in slots of said inner tube.

16. The diagnostic device according to claim 15, wherein said control slide is pivoted on the grip member and has an end outside of the grip member in order to be controlled by the operator.

17. The diagnostic device according to claim 16, wherein said control slide is pivoted on a control member which is pivoted on the grip member, said control member having an end external to the grip member in order to be controlled by the operator.

18. The diagnostic device according to claim 17, wherein guide profiles are provided within the grip member to allow the sliding of the end of the control slide.

19. The diagnostic device according to claim 12, wherein said means for generating a relative translation comprises a screw coupling between the inner tube being suitable to translate within the grip member and a handle being fitted on the proximal end of the grip member.

20. The diagnostic device according to claim 19, wherein the handle comprises a threaded tract that is suitable to be coupled with a threaded tract associated with the inner tube, the inner tube being fastened to the inside of the grip member such that only the relative translation thereof is allowed.

21. The diagnostic device according to claim 20, wherein the inner tube comprises an end portion being integral therewith and incorporating said threaded tract.

22. The diagnostic device according to claim 21, wherein said end portion comprises grooves being suitable to receive lugs of said grip member.

* * * * *